(12) United States Patent
McConnell et al.

(10) Patent No.: US 7,217,802 B2
(45) Date of Patent: May 15, 2007

(54) METHOD AND KIT FOR DETECTING, OR DETERMINING, 3,4-METHYLENE-DIOXYMETHAMPHETAMINE

(75) Inventors: Robert Ivan McConnell, Ballymena (GB); Elouard Benchikh, Antrim (GB); Stephen Peter Fitzgerald, Crumlin (GB); John Victor Lamont, Crumlin (GB)

(73) Assignee: Randox Laboratories Limited, Crumlin, County Antrim (IE)

( * ) Notice: Subject to any disclaimer, the term of this patent is extended or adjusted under 35 U.S.C. 154(b) by 413 days.

(21) Appl. No.: 10/326,742

(22) Filed: Dec. 20, 2002

(65) Prior Publication Data

US 2004/0121400 A1 Jun. 24, 2004

(30) Foreign Application Priority Data

Dec. 20, 2001 (EP) ................................. 01205058

(51) Int. Cl.
*C07K 1/13* (2006.01)
*C07K 16/00* (2006.01)
*G01N 37/00* (2006.01)
*G01N 33/532* (2006.01)
*G01N 33/533* (2006.01)
*G01N 33/53* (2006.01)
*C07D 317/46* (2006.01)

(52) U.S. Cl. .................. 530/403; 530/807; 530/388.9; 436/56; 436/544; 436/546; 436/815; 435/7.1; 435/810; 435/975; 549/444

(58) Field of Classification Search ................ 549/444; 435/961, 975, 7.1, 810; 530/388.9, 389.8, 530/403, 405, 807; 436/546, 545, 56, 544, 436/815; 424/175.1
See application file for complete search history.

(56) References Cited

U.S. PATENT DOCUMENTS 5,976,812 A 11/1999 Huber et al. ................. 435/7.1
2003/0207469 A1* 11/2003 Rouhani et al. ............ 436/518

FOREIGN PATENT DOCUMENTS

| EP | 0 399 184 A2 | 11/1990 |
| EP | 0 820 984 A1 | 1/1998 |
| EP | 1340981 A2 * | 9/2003 |
| GB | 2361473 A * | 10/2001 |

OTHER PUBLICATIONS

Thompson, W.C. et al., "Microwave-induced rapid preparation of fluoro-derivatives of amphetamine methamphetamine, and 3, 4-methylenedioxymethamphetamine for GC-MS confirmation assays", XP 002212535, *Clin. Chem.*, 1994, 40(9), 1703-1706, 2 pages.

(Continued)

*Primary Examiner*—Long V. Le
*Assistant Examiner*—Shafiqul Haq
(74) *Attorney, Agent, or Firm*—Woodcock Washburn LLP

(57) ABSTRACT

The invention provides a hapten, an immunogen comprising the hapten coupled to an antigenicity-conferring carrier material, a conjugate comprising the hapten coupled to a labelling agent, as well as, antibodies raised against the aforementioned immunogen and capable of binding with MDMA.

25 Claims, 11 Drawing Sheets

OTHER PUBLICATIONS

Uges En Medewerkers, D.R.A., "Determination of some xenobiotics in body fluids. XXVII. Amphetamine", XP 002212536, *Ziekenhuisfarmacie*, 1994, 10(1), 31-35, 2 pages.

Frison, G. et al., "Chromophoric Derivatives of Amphetamine Analogs: structural characterization by electron impact mass spectrometry", XP 002212537, *Org. Mass. Spectrom*, 1992, 27(11), 1284-1286, 1 page.

Noggle, F. Taylor, Jr. et al., "Spectrophotometric and Liquid chromatographic identification of 3,4-methylenedioxyphenylisopropylamine and its N-methyl and N-ethyl homologs", XP 002212538, *J-Assoc. Off. Anal. Chem*, 1986, 69(4), 681-6, 2 pages.

* cited by examiner

Figure -1: Chemical reaction for the preparation of haptens 7, 9 and 10

Figure 2: Competitive ELISA microtiter plate assays for MDMA

Figure 3: BSA Carrier Material

Figure 4: Immunogen 7

Figur 9

METHOD AND KIT FOR DETECTING, OR DETERMINING, 3,4-METHYLENE-DIOXYMETHAMPHETAMINE

The present invention relates to a method and kit for detecting, or determining, MDMA (3,4-methylenedioxymethamphetamine) and its methylenedioxy analogs.

By "detecting" is meant qualitatively analysing for the presence or absence of a substance.

By "determining" is meant quantitatively analysing for the amount of a substance.

By "methylenedioxy analogs" is meant N-(mono- or di-) alkylated (for example, N-methylated or N-ethylated) derivatives of methylenedioxyamphetamine (MDA).

The present invention describes the conjugation of novel hapten derivatives of MDMA, the haptens being covalently linked to an antigenicity-conferring carrier material or to a labelling agent, in order to produce immunogens or conjugates of the present invention, respectively. The present invention also describes how antibodies generated to these immunogens are employed in the development of a specific assay which can be used to detect, or to determine, MDMA or methylenedioxy analogs in biological fluids.

The method and kit of the present invention are intended to be highly specific for MDMA but will cross-react with methylenedioxy analogs such as 3,4-methylenedioxyethylamphetamine (MDEA). The method and kit of the present invention are intended not to significantly cross-react with the structurally related amphetamine and methamphetamine.

The structures of MDMA, MDEA and MDA are set out below:

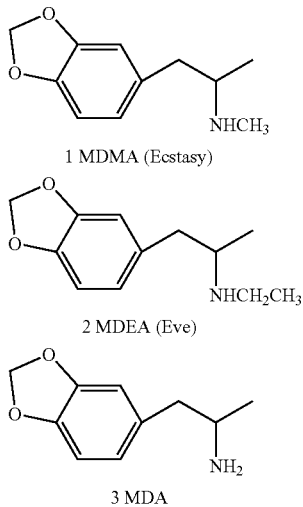

1 MDMA (Ecstasy)

2 MDEA (Eve)

3 MDA

MDMA and its methylenedioxy analogs are increasingly abused psychoactive drugs. MDMA's principal metabolite is MDA. However, 65% of MDMA is excreted unchanged in urine. The most frequently used compounds of the various clandestine products are 3,4-methylenedioxymethamphetamine (MDMA, 1), also known as Ecstasy, 3,4-methylenedioxyethylamphetamine (MDEA, 2), also known as Eve, and 3,4-methylenedioxyamphetamine (MDA, 3). These compounds exert their effects mainly on the serotonin system and, to a lesser extent, on the dopamine system. The popularity of methylenedioxyamphetamine derivatives can be attributed to their psychotropic effects.

Although MDMA, MDEA and MDA are generally regarded as relatively safe recreational drugs, it has become increasingly apparent that their use can be associated with many adverse effects and complications, some of which can lead to a fatal outcome. Furthermore, MDMA and MDA have been found to damage serotonin neurons in all experimental animals tested to date, and there are more serious concerns that human users are at risk of serotonin neurotoxicity, especially after the repeated use of high doses of the drug.

To date, the determination of MDMA and its methylenedioxy analogs in biological fluids has been based mainly on gas-chromatography-mass spectrometry (GC-MS), and HPLC. These chromatographic methods provide excellent sensitivity and selectivity but require derivatisation of MDMA and its methylenedioxy analogs. These methods are, in addition, too costly and time consuming for use as screening tools.

Specific binding reactions, such as antibody-antigen interactions, have been used extensively in immunoassays to detect a variety of substances present in biological fluids.

Thus, for example, radioimmunoassays could be used for the determination of the quantity of MDMA and its methylenedioxy analogs. Radioimmunoassays are very sensitive, but do require radionuclide tracers, for example $^{125}$I and $^{3}$H, and in some cases, a preliminary extraction step. There are no known RIAs for MDMA and its methylenedioxy analogs.

Enzyme-linked immunosorbent assays (ELISAs) are a nonradioactive alternative which are known for the qualitative and semi-quantitative determination of various amphetamine derivatives. However, the skilled man will appreciate that amphetamine derivatives lack the methylenedioxy ring of MDMA. Thus, for example, EP 0 399 184 A2 (Abbott Laboratories) describes the reagents, methods and kits for the detection and determination of amphetamine derivatives by fluorescence polarization immunoassay. EP 0 399 184 A2 prepares haptens, immunogens and antibodies from various amphetamines, all of which lack the methylenedioxy ring of MDMA. Example 20 of EP 0 399 184 A2 confirms that these reagents show less than 30% cross-reactivity, calculated as concentration found over concentration added, to MDMA, MDEA and MDA (see Table 2)). In addition, EP-A-820984 describes the preparation of haptens, immunogens and antibodies to amphetamine and methamphetamine, the haptens of which all lack the methylenedioxy ring of MDMA. Indeed, the haptens of EP-A-820984 are derivatised through the unfused phenyl ring of amphetamine, whereas, in contrast, MDMA and its methylenedioxy analogs contain a methoxylenedioxy ring fused to the phenyl ring.

Enzyme-linked immunosorbent assays (ELISAs) are a nonradioactive alternative which are known for the generic determination of amphetamines as a class. Specifically, both Emit (Registered Trade Mark) II Plus Monoclonal (supplied by Syva Company) and Cedia (Registered Trade Mark) DAU (supplied by Microgenetics/Roche) are ELAs for amphetamines. The respective cross-reactivities are 69% for MDMA (Cedia) when compared to 100% for D-methamphetamine and 14.3% for MDMA when compared to 100% for D,L-methamphetamine (Emit).

Enzyme-linked immunosorbent assays (ELISAs) are also known for the qualitative and semi-quantitative determination of MDMA and its methylenedioxy analogs.

Previously available MDMA immunoassays from Cozart Bioscience Limited (45 Milton Park, Abingdon, Oxfordshire, OX14 4RU, United Kingdom) are merely screening tests, which require confirmation by what Cozart denote as a "more specific" alternative chemical method—gas chromatography/mass spectrometry (GC-MS) is preferred. Thus, the Cozart methamphetamine EIA (available in October, 2001—now withdrawn) showed significant cross-reactivity, when compared to 100% for methamphetamine, against MDMA (758–1250%), MDEA (50–100%) and N-methyl-1-(3,4-methylenedioxyphenyl)-2-butamine (MBDB) (150–200%), whilst the Cozart MDMA EIA (available in October, 2001—now withdrawn) showed significant cross-reactivity, when compared to 100% for MDMA, with D-methamphetamine (52–80%) and DL-MBDB (10.4–20%). These two Cozart assays have now been replaced by a single Cozart methamphetamine kit, which exhibits a cross-reactivity of 43–49% for MDMA, when compared to 100% for methamphetamine.

The cross-reactivity data for the various assays mentioned above have been recalculated relative to 100% for MDMA and these data are schematically presented in the table below:

significantly cross-react with both d-amphetamine and (+)-methamphetamine. By "not significantly" is meant (for each of d-amphetamine and (+)-methamphetamine) a cross-reactivity of less than about 7.5%, preferably less than about 5%, more preferably less than about 1%, still more preferably less than about 0.5%, most preferably less than about 0.25%, when compared to 100% for MDMA. In order to achieve such specificity, the haptens described in the present invention are generated by derivatisation at the N-position of MDMA.

It is a further object of a preferred embodiment of the present invention to develop antibodies capable of binding with, as a structural epitope, the intact methylenedioxy ring of MDMA and methylenedioxy analogs.

| Compound | Cozart Amphetamine | Cozart Methamphetamine and MDMA | Cozart Methamphetamine | Cozart MDMA | CEDIA | Emit |
|---|---|---|---|---|---|---|
| MDMA | 100 | 100 | 100 | 100 | 100 | 100 |
| D-Amphetamine | 1,428 | 1.52 | 1 | 0.2–0.43 | 146.5 | 917 |
| D,L-Amphetamine | — | — | — | — | 84.1 | 545.6 |
| L-Amphetamine | — | — | — | — | 4.35 | 120.13 |
| D-Methamphetamine | — | 217 | 10 | 52–80 | 145 | — |
| D,L-Methamphetamine | — | — | — | — | 94.25 | 699.7 |
| L-Methamphetamine | — | — | — | 4–22 | 17.4 | 378.7 |
| MDA | 208488–304164 | 0.87 | 0.36 | 0.3–0.74 | 2.76 | 430.1 |
| MDEA | 228.5 | 10.85 | 5–10 | 7.0–13.0 | — | — |
| MBDB | — | 319–334.2 | 15–20 | 10.4–20 | — | — |

SUMMARY OF THE INVENTION

The present invention describes a hapten derivatised with a crosslinker at the N-position of MDMA.

The present invention provides an immunogen comprising the aforementioned hapten, coupled to an antigenicity-conferring carrier material, as well as, conjugates comprising the aforementioned hapten covalently bonded to a detectable labelling agent. In addition, the present invention concerns antibodies raised against the aforementioned immunogens.

Finally, the present invention relates to methods and kits for detecting or determining MDMA and N-alkylated derivatives of methylenedioxyamphetamine in biological fluids.

The antibodies of the present invention do not significantly cross-react with amphetamine and methamphetamine.

OBJECTS OF THE INVENTION

It is an object of the invention to overcome some or all of the disadvantages of the prior art, or to provide an alternative thereto.

It is an object of a preferred embodiment of the invention to provide a method and a kit for detecting, or determining the quantity of, MDMA and its methylenedioxy analogs.

Figure 2:
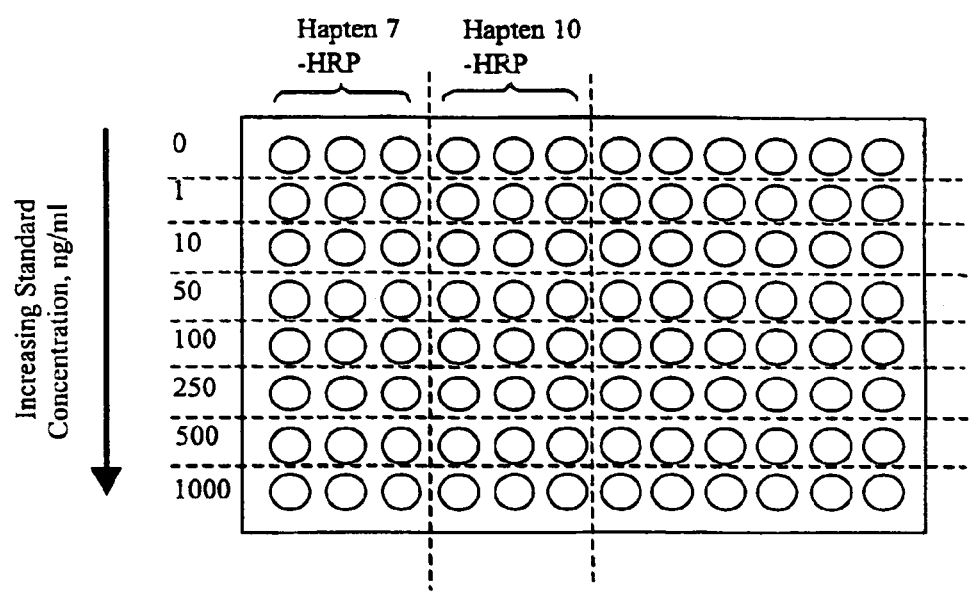

The aim of the present invention is to overcome the lack of specificity problems associated with known immunoassays for MDMA, by preparing a highly specific antibody to MDMA and its methylenedioxy analogs, which will not FIG. 2 shows a diagram of the Competitive ELISA microtiter plate assays for MDMA.

Figure 3:
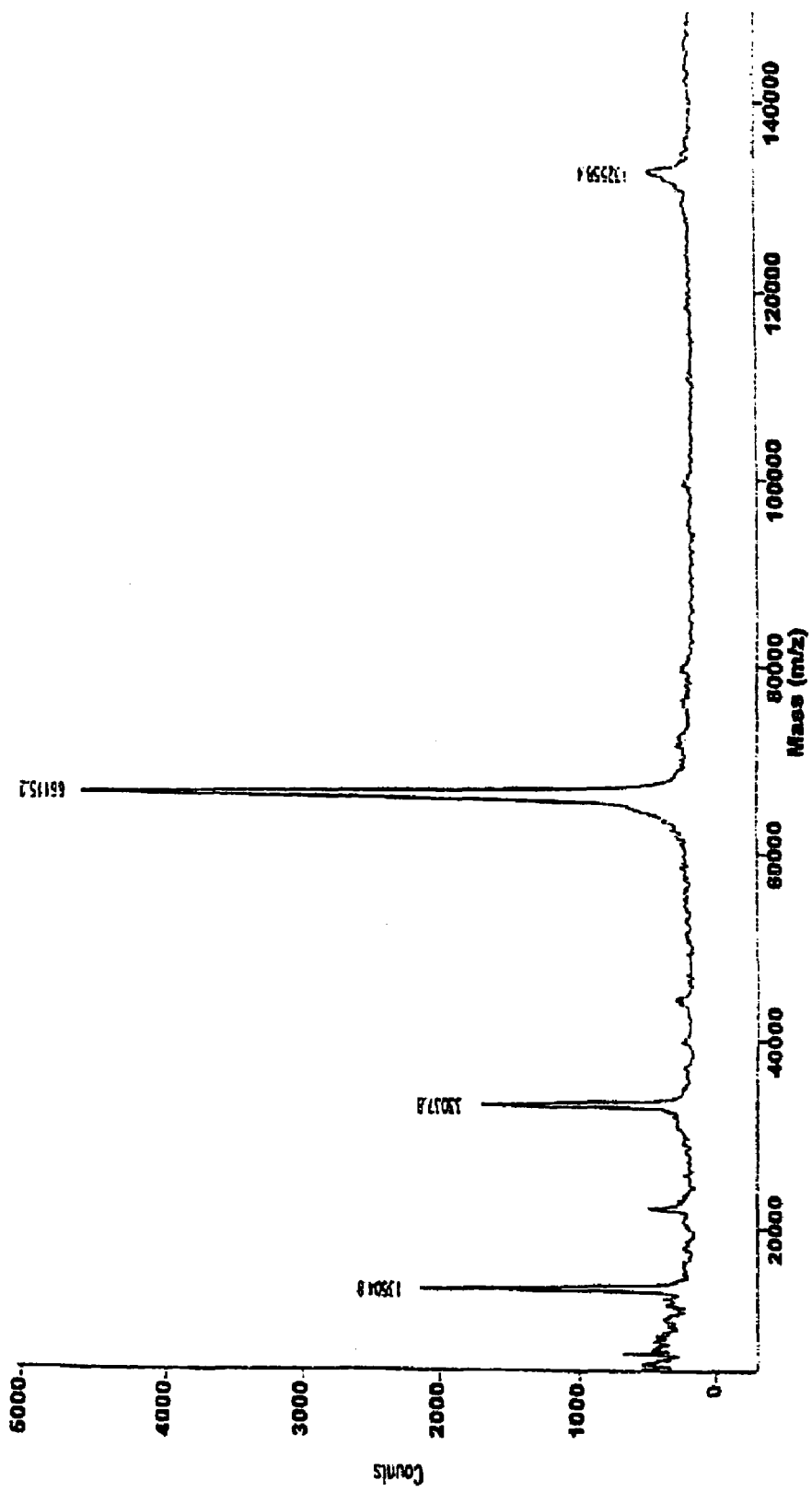

FIG. 3 shows a MALDI-TOF mass spectrometry analysis of BSA carrier material.

Figure 4:
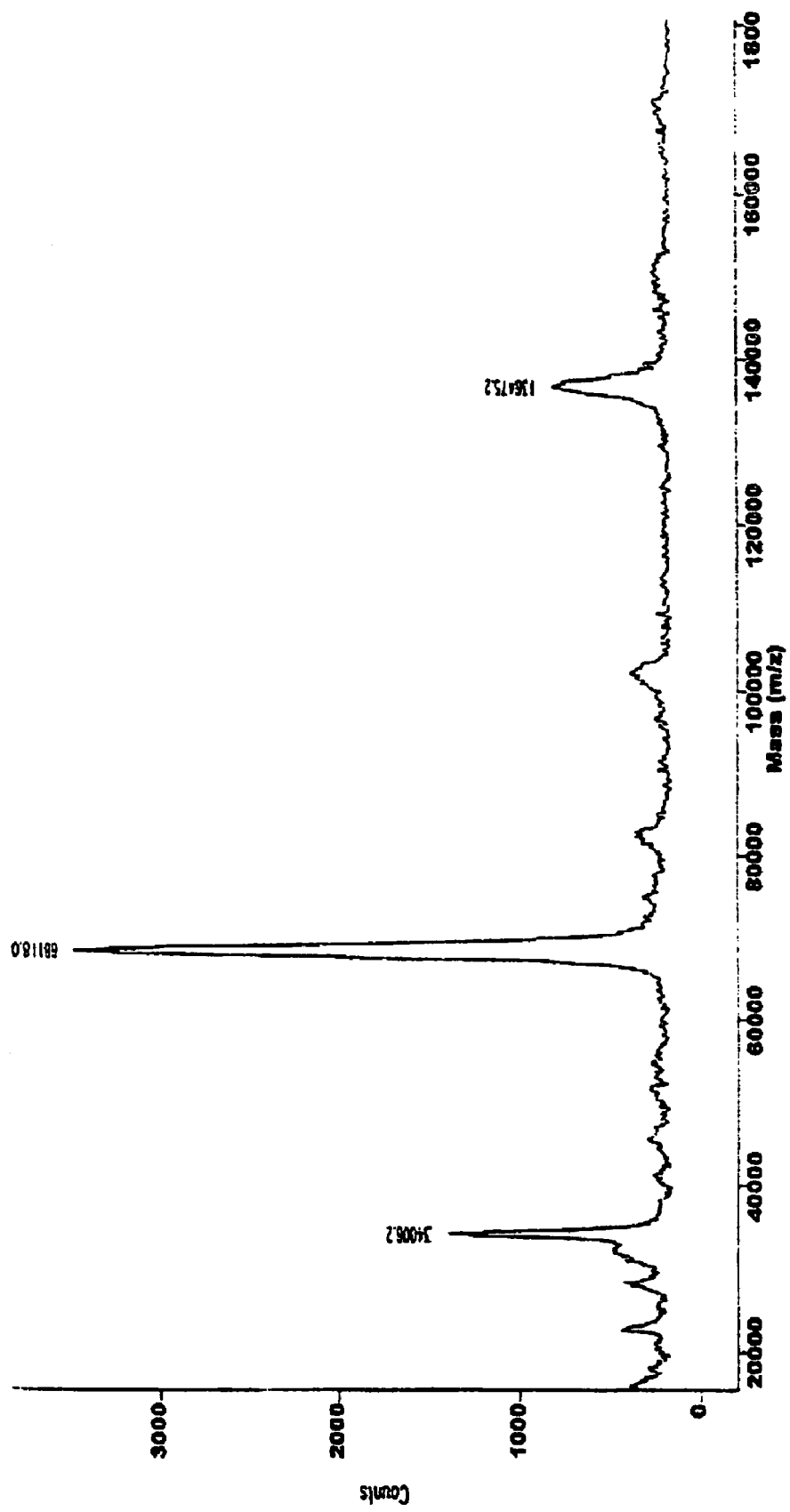

FIG. 4 shows a MALDI-TOF mass spectrometry analysis of Immunogen 7.

Figure 5:
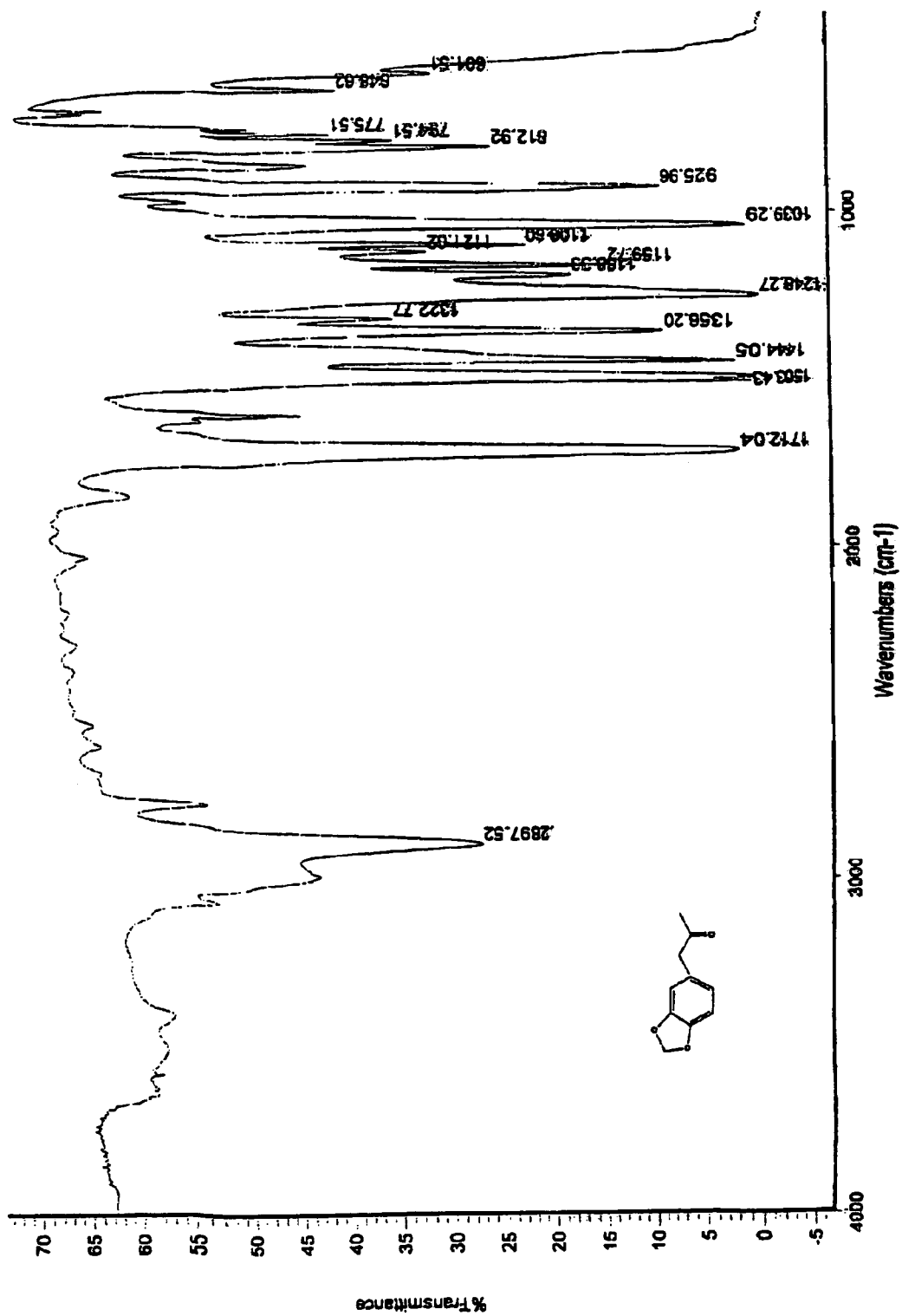

FIG. 5 shows an FT-IR tracing of (3,4-methylenedioxy) phenylacetone.

Figure 6:
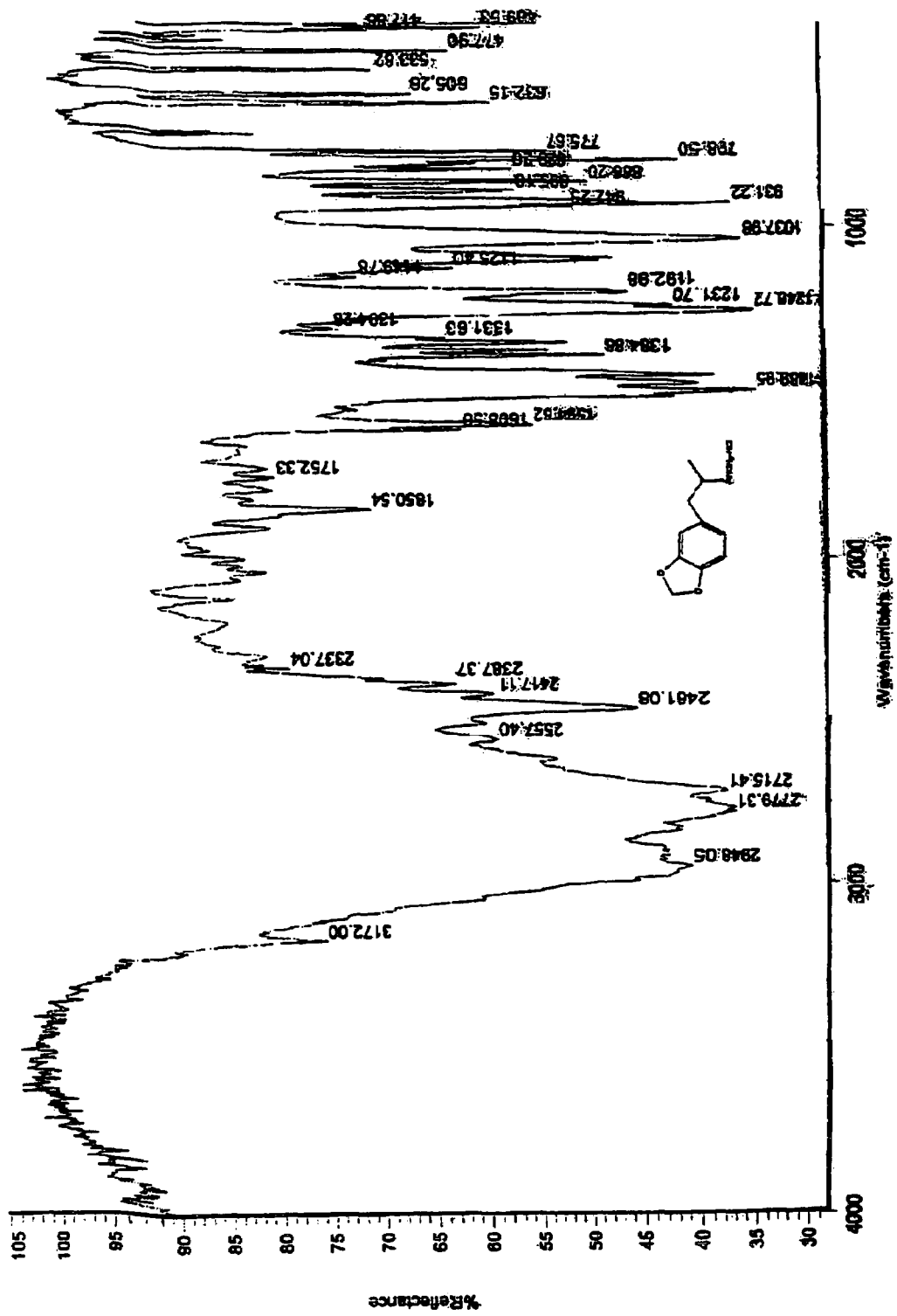

FIG. 6 shows an FT-IR tracing of 3,4-methylenedioxymethamphetamine.

Figure 7:
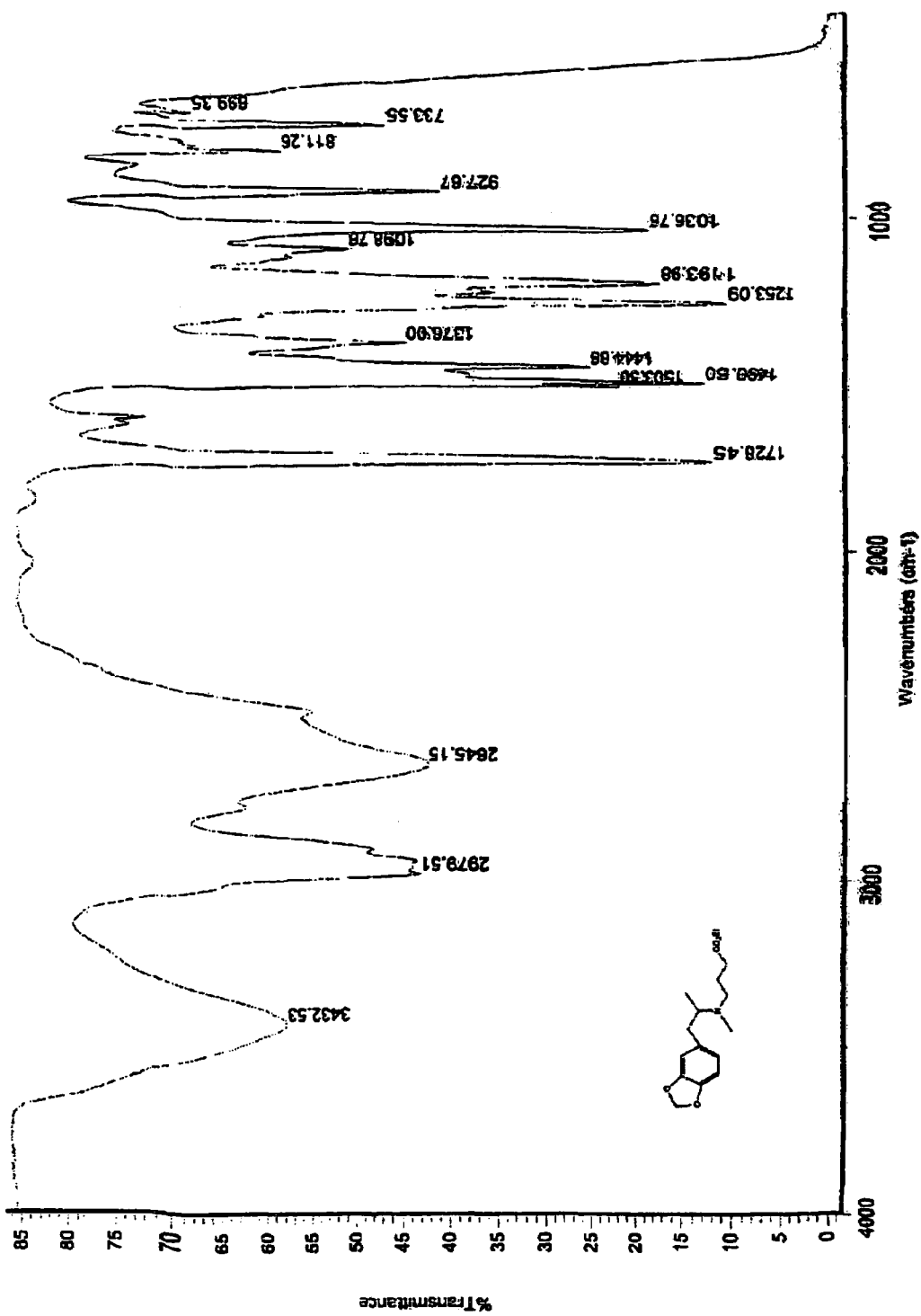

FIG. 7 shows an FT-IR tracing of [ethyl-N-(3'-carboxypropyl)]-3,4-methylenedioxymethamphetamine.

Figure 8:
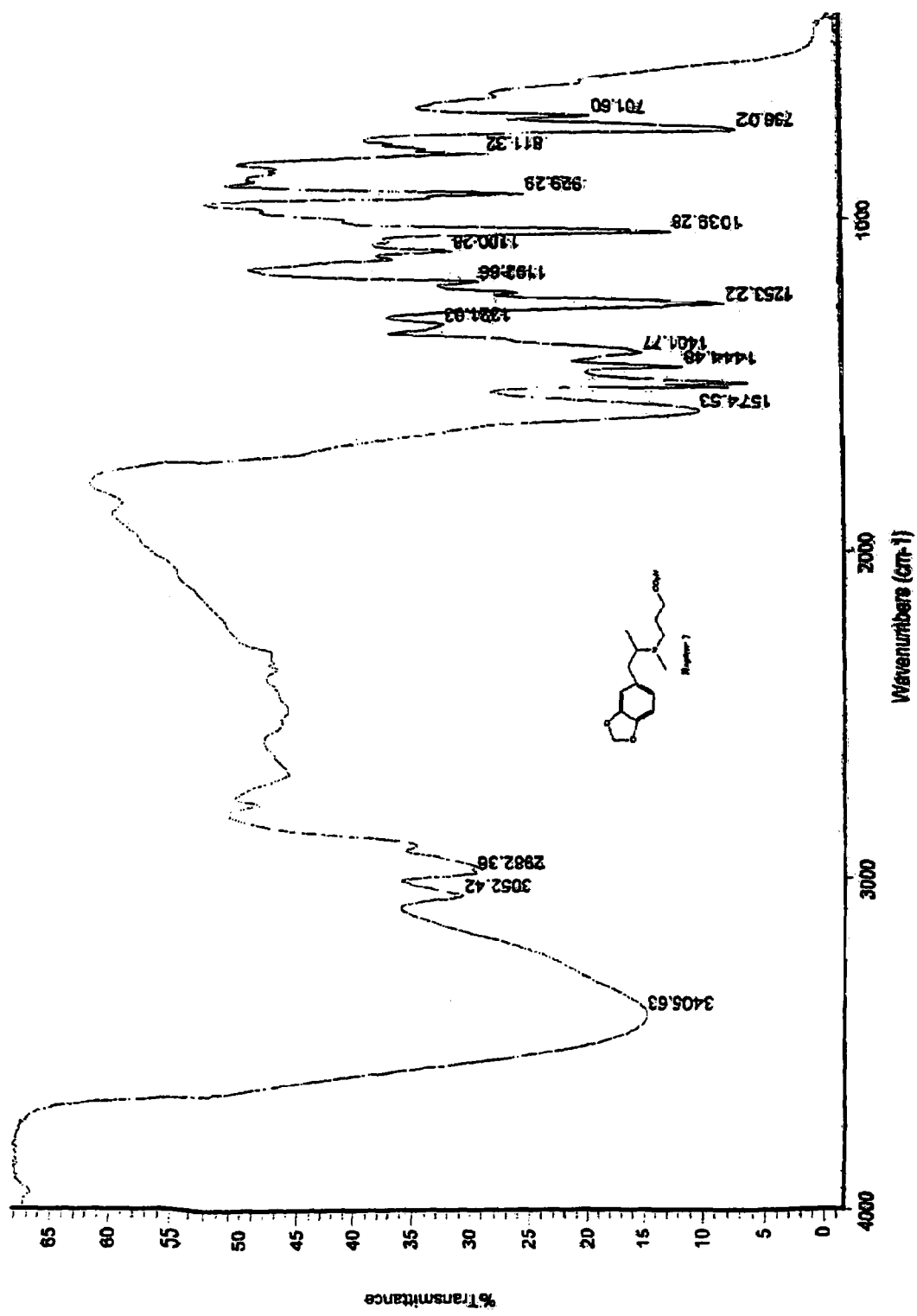

FIG. 8 shows an FT-IR tracing of N-(3'-carboxypropyl)-3,4-methylenedioxymethamphetamine.

Figure 9:
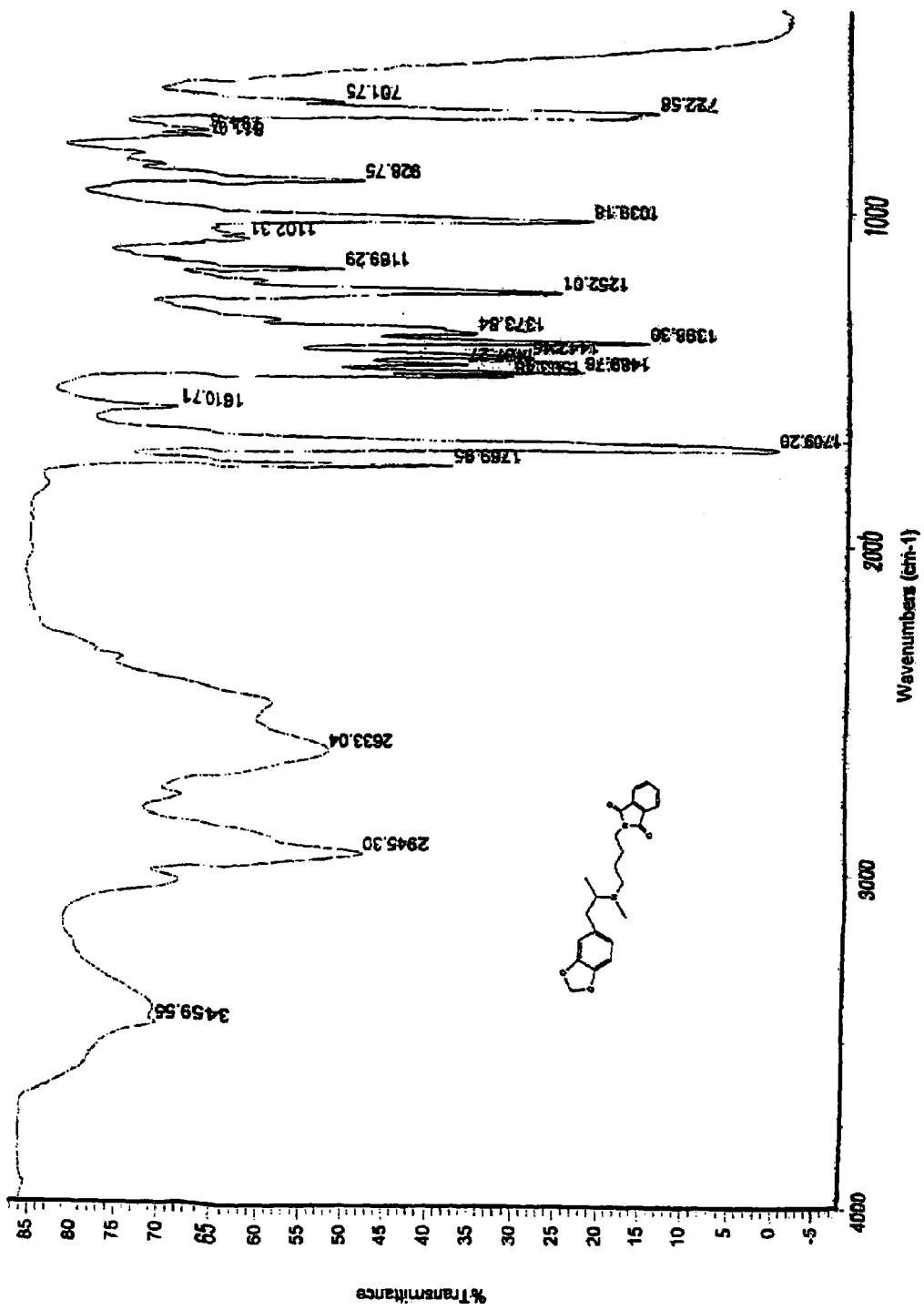

FIG. 9 shows an FT-IR tracing of N-(4'-butylphthalimido)-3,4-methylenedioxymethamphetamine.

Figure 10:
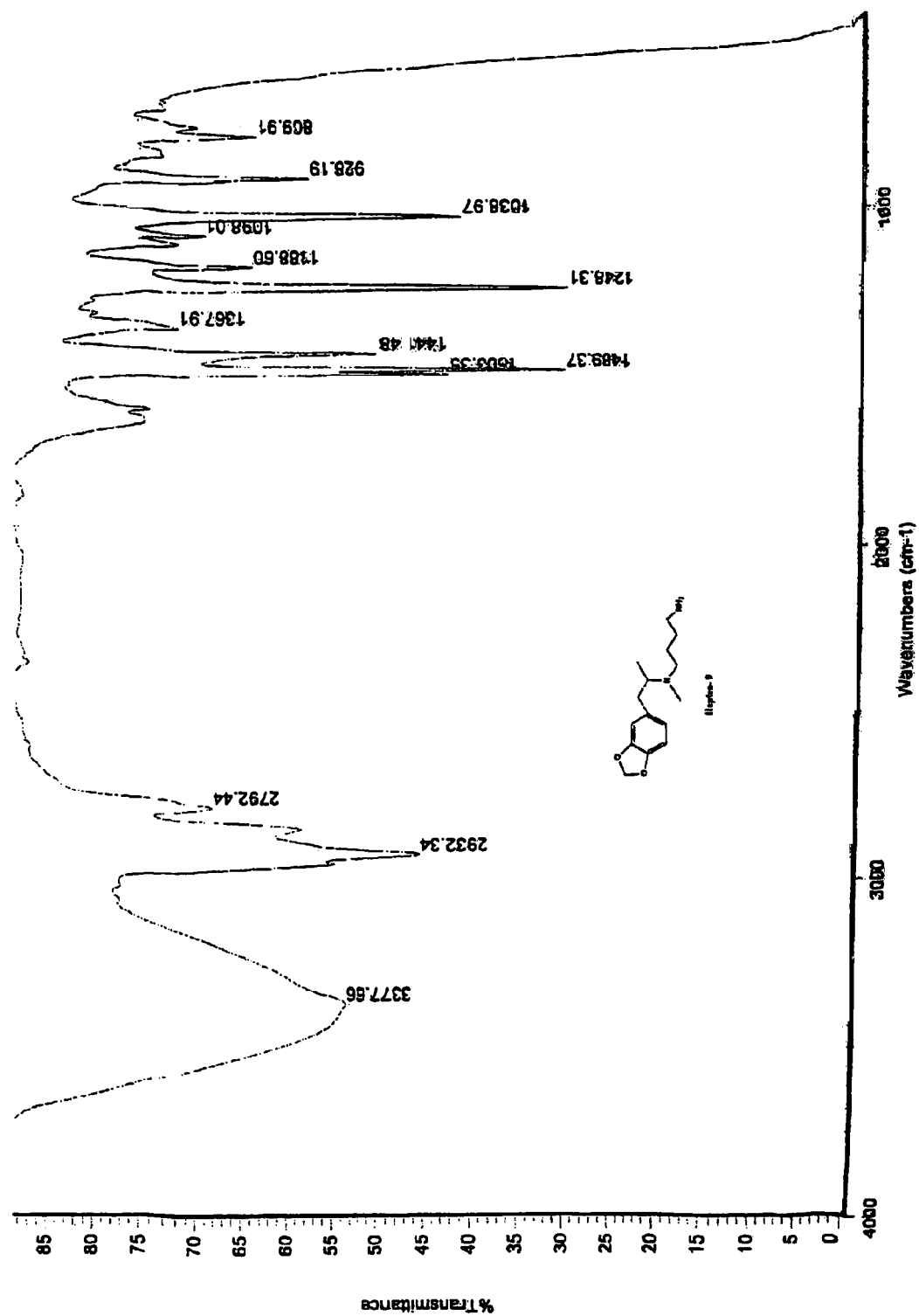

FIG. 10 shows an FT-IR tracing of N-(4'-aminobutyl)-3,4-methylenedioxymethamphetamine dihydrochloride.

Figure 11:
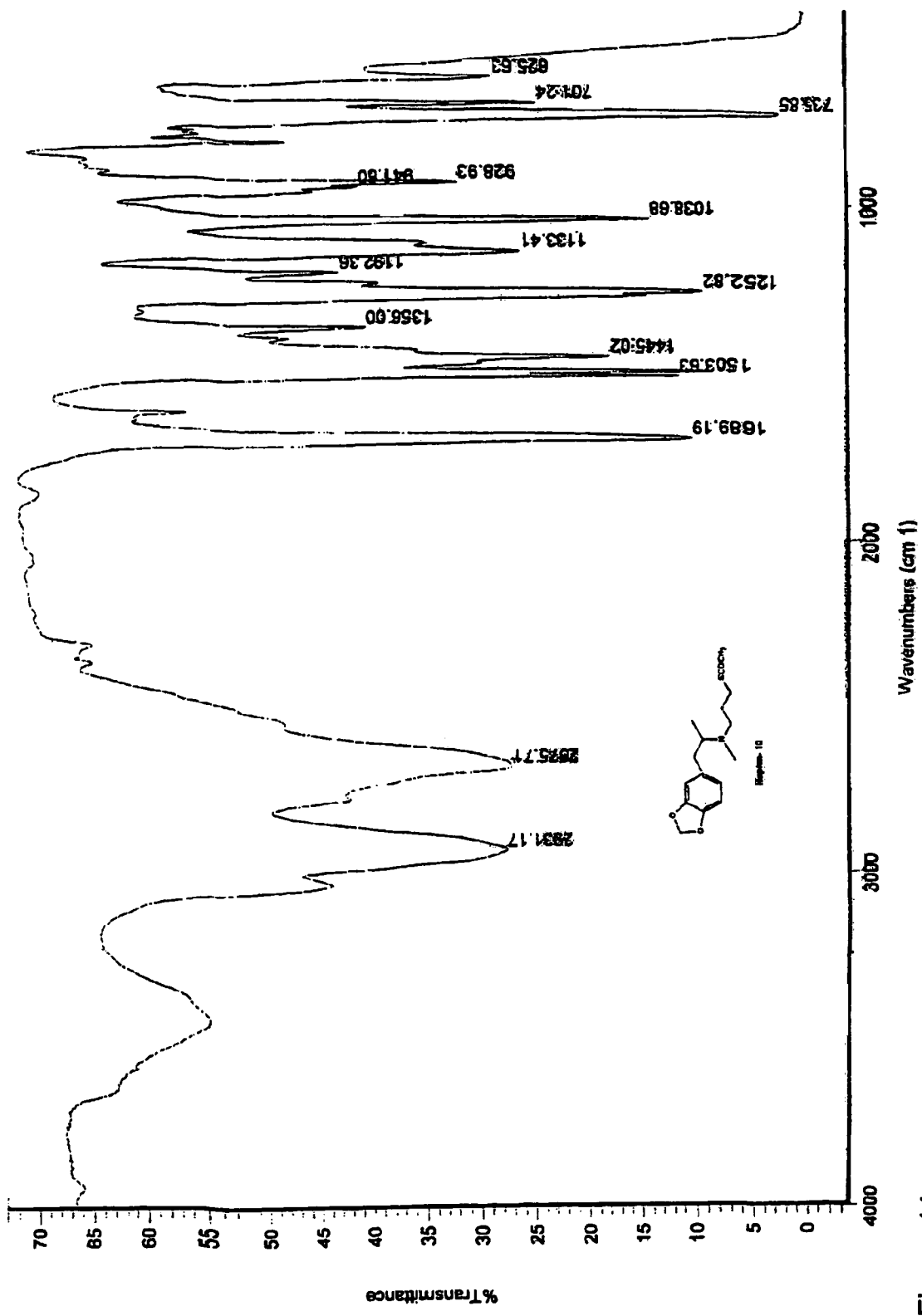

FIG. 11 shows an FT-IR tracing of N-(3'-acetylthiopropyl)-3,4-methylenedioxymethamphetamine.

DETAILED DESCRIPTION OF INVENTION

The invention describes a hapten wherein the hydrogen bonded to the N of MDMA is replaced by (in other words, derivatised with) a crosslinker.

In a first aspect, the invention provides an immunogen of the following structural formula:

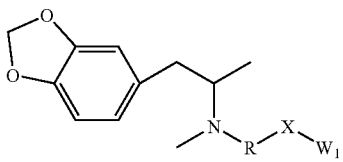

wherein R is a bivalent link and X is a terminal group (or $W_1$ linker), and wherein $W_1$ is an antigenicity-conferring carrier material. Preferably, the carrier material is a protein, a protein fragment, a synthetic polypeptide or a semi-synthetic polypeptide.

In a second aspect, the invention provides a conjugate of the following structural formula:

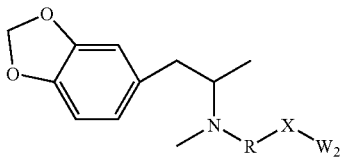

wherein R is a bivalent link and X is a terminal group (or $W_2$ linker), and wherein $W_2$ is a detectable labelling agent. Preferably, the labelling agent is selected from an enzyme, a luminescent substance, a radioactive substance, or a mixture thereof. More preferably, the labelling agent is an enzyme, preferably a peroxidase, most preferably horseradish peroxidase (HRP). Alternatively, or additionally, the luminescent substance may be a bioluminescent, a chemiluminescent or a fluorescent material.

In the first and second embodiments, the crosslinker is —R—X—.

Preferably, R comprises:

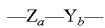

wherein Z is a substituted or unsubstituted, straight or branched chain, saturated or unsaturated alkylene moiety or a substituted or unsubstituted arylene, preferably phenylene, moiety; Y is a substituted or unsubstituted, straight or branched chain, saturated or unsaturated alkylene moiety; a is 0 or 1 and b is 0 or 1, with the proviso that a and b cannot both be 0. In other words, one of Z and Y or, alternatively, both of Z and Y must be present in R. More preferably, b is 0, a is 1 and Z is a $C_{1-6}$, substituted or unsubstituted, straight or branched chain, saturated or unsaturated alkylene moiety.

Most preferably, Z is a $C_{3-4}$ unsubstituted, straight chain, saturated alkylene moiety.

Advantageously, X, before reaction with $W_1$ or $W_2$ is selected from a carboxylic acid or an ester thereof, an amine, a maleimide, a halocarboxylic acid or an ester thereof, a thiocarboxylic acid or an ester thereof, an aldehyde, a pyridyldithio or a vinylsulphone moiety.

More advantageously, X, before reaction with $W_1$ or $W_2$, is selected from a carboxylic acid (—COOH), an amine (—NH$_2$) and a thiocarboxylate ester (—S—CO—CH$_3$).

In a further aspect, the present invention concerns antibodies raised against the immunogen of the first aspect of the present invention, the antibodies being capable of binding with at least one structural epitope of MDMA, preferably with the intact methylenedioxy ring structural epitope. The antibodies have specificity for MDMA and other methylenedioxy analogs. The antibodies should have a cross-reactivity of less than 10%, preferably less than 5%, more preferably less than 1%, most preferably less than 0.5% for the structurally related amphetamine and methamphetamine. Preferably, the antibodies are fixed on a backing substrate. Preferably, the antibodies are polyclonal. Alternatively, the antibodies are monoclonal.

The invention further provides a process of preparing the antibodies, the process comprising the steps of immunising an animal, preferably a vertebrate animal, most preferably a mammalian animal, by repeated administration of an immunogen according to the first aspect of the present invention, and collecting the resulting serum from the immunised animal. Preferably, the process further comprises fixing said serum antibodies to a backing substrate, preferably a solid support, most preferably a polystyrene solid support. Antibodies prepared in accordance with this process are polyclonal.

In a still further aspect, the present invention comprises a method for detecting or determining MDMA and its methylenedioxy analogs in a sample, the method comprising contacting the sample with the conjugate of the present invention, or a mixture thereof, and with antibodies of the present invention, or a mixture thereof; detecting, or determining the quantity of, bound conjugate; and deducing from a calibration curve the presence of, or the amount of, MDMA and its methylenedioxy analogs in the sample.

In a further aspect, the invention includes a kit for detecting or determining MDMA and its methylenedioxy analogs, the kit including the conjugate of the present invention, or a mixture thereof and the antibodies of the present invention, or a mixture thereof. The kit may optionally include instructions for the use of said conjugates and said antibodies for detecting or determining MDMA and its methylenedioxy analogs in a sample.

Preferably, the sample is a solution, such as a biological fluid. More preferably, the sample is serum or urine. Most preferably, the sample is a solution from a human patient.

In the method and kit of the present invention, it is preferred that the respective crosslinkers (of the immunogen and the conjugate) are different.

In a further aspect, the present invention involves use of the conjugates according to the present invention, or a mixture thereof, with the antibodies according to the present invention, or a mixture thereof, to detect or determine MDMA and its methylenedioxy analogs in test samples such as biological fluids.

Preparation of Haptens

Figure 1:
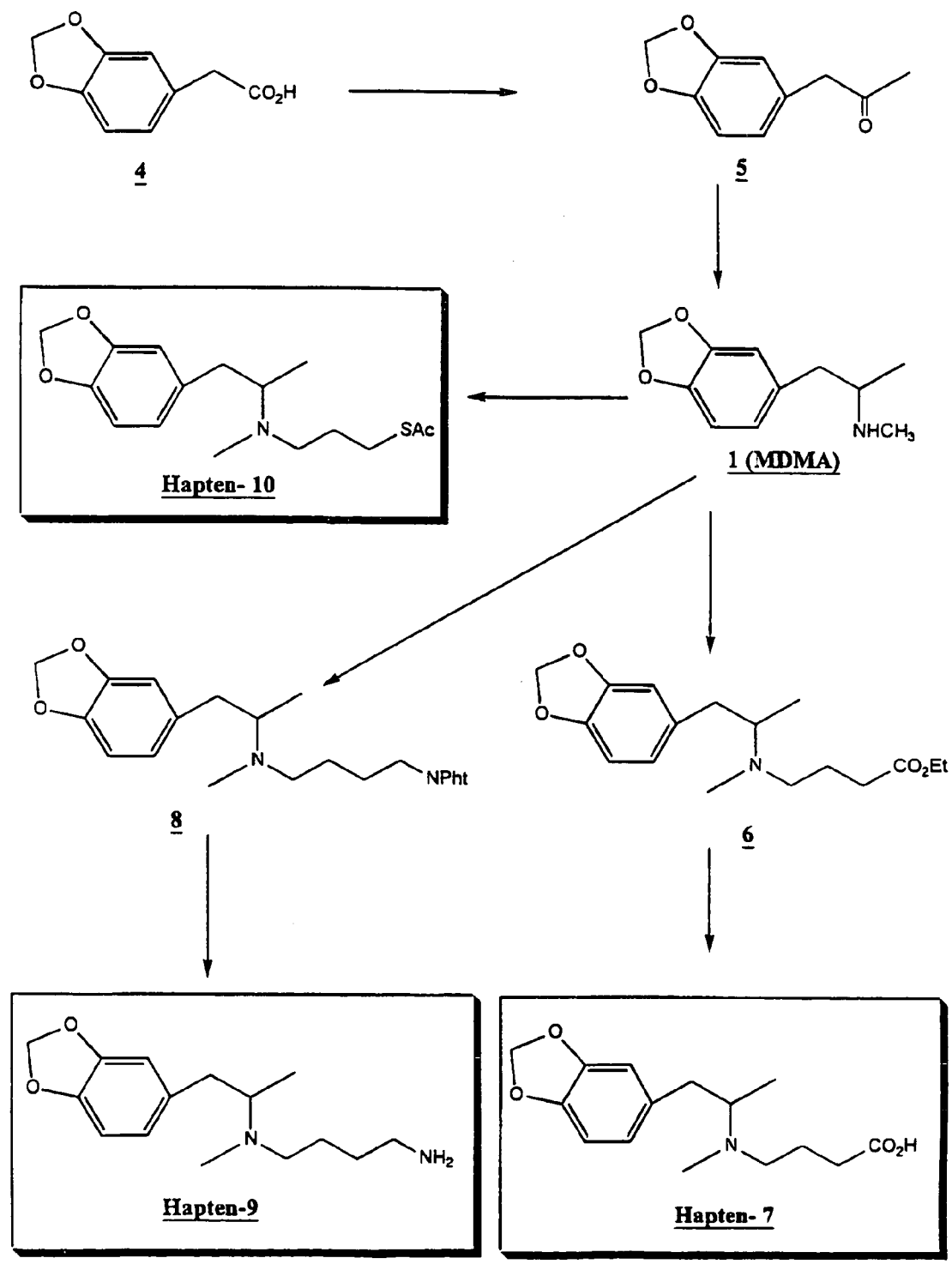
FIG. 1 shows the chemical reaction scheme for the preparation of Haptens 7, 9 and 10.

The hapten derivatives N-(3'-carboxypropyl) MDMA (compound 7), N-(4'-aminobutyl) MDMA (compound 9) and N-(3'-acetylthiopropyl) MDMA (compound 10) are prepared as outlined in FIG. 1. First is the preparation of 3,4-methylenedioxymethamphetamine (compound 1) from 3,4-(methylenedioxy)phenylacetic acid (compound 4) in two steps: reaction of compound 4 with acetic anhydride/pyridine and the subsequent hydrolysis of the intermediate with concentrated HCl in ethanol at reflux gives 3,4-(methylenedioxy)phenylacetone (compound 5). The reaction of compound 5 with methylamine hydrochloride in methanol in the presence of triethylamine and sodium cyanoborohydride gives MDMA (compound 1) in good yield. The haptens 7, 9 and 10 are obtained from compound 1 as follows:

Hapten 7

The reaction of compound 1 with ethyl-4-bromobutyrate in acetonitrile at reflux in the presence of catalytic potassium iodide gives the ester-compound 6. The hapten 7, N-(3'-carboxypropyl) MDMA, is obtained after saponification of compound 6 by potassium hydroxide in tetrahydrofuran (THF)/water.

Hapten 9

The reaction of compound 1 with (N-(4-bromobutyl) phthalimide in ethanol at reflux, followed by hydrolysis of the phthalimide group by hydrazine hydrate in methanol at reflux gives the hapten N-(4'-aminobutyl) MDMA (compound 9).

Hapten 10

The hapten 10 [N-(3'-acetylthiopropyl) MDMA] is prepared by reaction of MDMA (compound 1) with iodopropylthioacetate in ethanol at reflux.

Preparation of Immunogens and Conjugates

Although the MDMA haptens provide defined structural epitopes (the intact methylenedioxy ring), they are not in themselves immunogenic and therefore need to be conjugated to carrier material which will elicit an immunogenic response when injected into a host animal. Suitable carrier materials include proteins such as albumins, serum proteins e.g. globulins, ocular lens proteins and lipoproteins. Illustrative protein carriers include bovine serum albumin, egg ovalbumin, bovine gamma globulin, thyroxine binding globulin, keyhole limpet haemocyanin (KLH) etc. Alternatively, synthetic poly(amino acids) having a sufficient number of available amine groups such as lysine may be employed, as may other synthetic or natural polymeric materials bearing reactive functional groups. In particular, carbohydrates, yeasts or polysaccharides may be conjugated to the hapten to produce an immunogen.

Each hapten can also be covalently linked to a labelling agent such as an enzyme (for example, horse radish peroxidase), a substance having fluorescent properties or a radioactive label to produce conjugates (or detection reagents) for use in the immunoassays. The fluorescent substance may be, for example, a monovalent residue of fluorescein or a derivative thereof.

In order to confirm that adequate conjugation of hapten to carrier material has been achieved, prior to immunisation, each immunogen is evaluated using matrix-assisted UV laser desorption/ionization time-of-flight mass spectrometry (MALDI-TOF MS). In the case of the preferred carrier material, bovine serum albumin, a minimum of 6 molecules of hapten per carrier molecule is preferred.

In preparing conjugates or immunogens with haptens where a thiol group is present such as, for example, hapten 10, maleimide, halo, pyridyldithio or vinylsulphone groups must first be introduced to the labelling agent or carrier material, respectively, using heterobifunctional linkers such as, but not limited to:

N-(γ-maleimidobutyryloxy)succinimide ester (GMBS); succinimidyl 4-(N-maleimidomethyl)cyclohexane-1-carboxylate (SMCC); (m-maleimidobenzoyl)-N-hydroxysuccinimide (MBS); succinimidyl 4-(p-maleimidophenyl)butyrate (SMPB); N-succinimidyl(4-iodoacetyl) aminobenzoate (SIAB); bromoacetyl-glycine N-hydroxysuccinimide; N-succinimidyl 3-(2-pyridyldithio) propionate (SPDP); vinylsulphone (Pierce Chemical Company, USA). The thus-modified labelling agent or carrier material, can then be conjugated via the thiol group present on the hapten, such as hapten 10. For haptens without a thiol group present, such as haptens 7 and 9, conjugation is performed without prior-modification of labelling agent or carrier material, as appropriate, using standard methods of conjugation such as 1-ethyl-3-(3-dimethylaminopropyl)carbodiimide (EDC) or mixed anhydride. Specifically, hapten 7 is conjugated to, for example, HRP by EDC and hapten 9 by sodium metaperiodate, followed by reduction of the Schiff base with sodium cyanoborohydride.

Preparation of Antisera

In order to generate polyclonal antisera, the immunogen is mixed with Freund's Adjuvant and the mixture is injected into a host animal, such as a rabbit, sheep, mouse, guinea pig or horse. Further injections (boosts) are made and serum is sampled for evaluation of antibody titer. When the optimal titer has been reached, the host animal is then bled to yield a suitable volume of specific antiserum. The degree of antibody purification required depends on the intended application. For many purposes, there is no requirement at all for purification, however, in other cases, such as where the antibody is to be immobilized on a solid support, purification steps can be taken to remove undesired material and eliminate non-specific binding.

The specific antibodies of the present invention are useful as reagents in immunoassays for the detection, or for the determination, of MDMA and methylenedioxy analogs in biological fluids.

General Procedure for MALDI-TOF Analysis of Immunogens.

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of Sinapinic acid and bovine serum albumin (Fluka) was used as an external calibrant. FIG. 3 of the accompanying drawings shows the analysis for BSA carrier material. As will be seen, a major signal was present which indicates an average protonated mass for this sample of m/z 66,115. The signals observed at m/z 33,038 and 132,558 are consistent with the major observed component in a doubly-charged form and dimer form, respectively. Further signals were observed including that at m/z 13,505.

In the following Examples, percentages are to be taken as percentages (volume/volume), unless otherwise specified.

EXAMPLES

Example-1

Preparation of (3,4-methylenedioxy)phenylacetone 5

(3,4-Methylenedioxy)phenylacetic acid (compound 4) (15 g, 0.0832 mol) was dissolved in acetic anhydride (73.5 ml) and pyridine (33.75 ml) and the mixture refluxed for 16 hours. After cooling, the solvents were removed in vacuo (temperature should be kept as low as possible) and the residue was taken up in dry ethanol (58.5 ml), conc. HCl (5.63 ml) was added and the mixture was refluxed for 2 hours.

Water (150 ml) was added and extracted with dichloromethane (3×150 ml). The combined organic extracts were dried over sodium sulphate, filtered and the solvent removed. The residue was purified by column chromatography (Silica gel, 10%–20% ethyl acetate in hexane) to give 11.25 g (77% yield) of (3,4-methylenedioxy)phenylacetone (compound 5) as an orange oil.

FT-IR (film, neat): 1711.67 cm$^{-1}$ (FIG. 5)

Example-2

Preparation of 3,4-methylenedioxymethamphetamine (MDMA) 1

Compound 5 (4 g, 0.022 mol) was dissolved in methanol (100 ml) and to this stirred solution was added, methylamine hydrochloride (15.16 g, 0.22 mol) and triethylamine (6.76 ml, 0.049 mol). Sodium cyanoborohydride (1.41 g, 0.022 mol) in methanol (10 ml) was added in one portion and the reaction mixture stirred at room temperature overnight.

The solvents were removed in vacuo, water (50 ml) followed by 1N HCl (50 ml) was added and the mixture washed with diethyl ether (100 ml). The aqueous phase was basified to pH 12–13 with 2N NaOH and extracted with ethyl acetate (3×100 ml). The combined organic extracts were dried over sodium sulphate, filtered and the solvent was removed to give crude MDMA (compound 1) free base as brown oil in good yield.

The crude product obtained was used without further purification.

FT-IR (film, neat): 3172, 2779.3, 2715.4, 1246.7 and 1037.9 cm$^{-1}$ (FIG. 6)

Example-3

Preparation of [ethyl N-(3'-carboxypropyl)]-3,4-methylenedioxymethamphetamine 6

Crude compound 1 (2.4 g) was taken up in dry acetonitrile. Ethyl 4-bromobutyrate (2.426 g, 0.12 mol) was added followed by potassium iodide (200 mg) and the resulting mixture refluxed for 4–5 hours. After cooling, the solution was filtered and the solvent removed in vacuo.

Purification of the crude product obtained by chromatography on silica gel (5% methanol in chloroform) gave 1.356 g of a pale orange oil of ester 6.

FT-IR (film, neat): 2645.15, 1728.45, 1490.6, 1253.0 and 1036.7 cm$^{-1}$ (FIG. 7).

Example-4

Preparation of N-(3-Carboxypropyl)-3,4-methylenedioxymethamphetamine -Hapten 7

Ester 6 (1.356 g) was taken up in tetrahydrofuran (10 ml) and water (10 ml), potassium hydroxide (0.371 g) was added and the mixture was stirred at room temperature until TLC (5% methanol (MeOH)/chloroform) indicated the reaction was complete.

The mixture was neutralised by the addition of 1N HCl and reduced to dryness in vacuo. The residue was treated with ethanol (20 ml) and the insoluble inorganic material filtered off. The solvent was removed in vacuo and the residue recrystallised from acetonitrile to give 0.529 g of hapten 7 as white foam.

FT-IR(KBr): 3405.63, 1574.53 (br), 1253.22 and 1039.2 cm$^{-1}$ (FIG. 8) m.p (acetonitrile): 37–40° C.

Example-5

Preparation of N-(4-butylphthalimido)-3,4-methylenedioxymethamphetamine 8

Crude MDMA 1 (2.35 g) was taken up in absolute ethanol (20 ml), N-(4-bromobutyl)phthalimide (3.14 g, 0.0128 mol) was added and the resulting mixture refluxed for 4–5 hours. After cooling at room temperature, the solvent was removed in vacuo and the residue chromatographed on silica gel, using 10% methanol in chloroform, to give 2.013 g of compound 8 as a light brown oil.

FT-IR (film, neat): 2633.0, 1709.2, 1398, 1252 and 1039.1 cm$^{-1}$ (FIG. 9)

Example-6

Preparation of N-(4'-Aminobutyl)-3,4-methylenedioxymethamphetamine Dihydrochloride-Hapten 9

Compound 8 from Example-5 (2.013 g, 0.005 mol) was taken up in dry methanol (50 ml) and hydrazine hydrate (0.246 g) added. The mixture was refluxed for 2 hours, after which a further 0.138 g of hydrazine hydrate was added and reflux continued for a further 2 hours. The mixture was then cooled at room temperature and the solvents removed in vacuo to leave a brown oil.

The oil was taken up in the minimum amount of water and treated with approximately 10 ml of 1N HCl (pH 4–5). The precipitate was filtered off and the filtrate basified to pH 12–13 with 6N NaOH and extracted with dichloromethane (4×50 ml). The combined organic extracts were dried over sodium sulphate, filtered and the solvent removed to leave the free base as pale brown oil.

The oil was treated with 2N HCl gas in diethyl ether (20 ml) and stirred for 1–2 hours. The precipitate was collected, washed with cold diethyl ether and dried to give 0.877 g of N-(4'-aminobutyl)MDMA hydrochloride (hapten 9) as an off-white solid.

FT-IR (KBr): 3377.66, 2792.44, 1489.3 and 1038.97 cm$^{-1}$ (FIG. 10) m.p: 232–234° C.

Example-7

Preparation of N-(3'-Acetylthiopropyl)-3,4-methylenedioxymethamphetamine-Hapten 10

Crude MDMA 1 (2.98 g, 0.0154 mol) was taken up in absolute ethanol (50 ml), iodopropylthioacetate (5.65 g, 0.023 mols) was added and the resulting mixture was refluxed for 16 hrs. The mixture was then cooled at room temperature and the ethanol was removed in vacuo. The crude dark mixture obtained was purified by chromatography (silica gel; 10% methanol in chloroform) to give 2.2 g of N-(acetylthiopropyl) MDMA (hapten 10), as a clear yellow oil.

FT-IR (film, neat): 2931.1, 2675.7, 1689.2, 1252.8, 1038.7 and 735.8 cm$^{-1}$ (FIG. 11)

Example-8

Conjugation of Hapten 7 to BSA: Immunogen 7

To a solution of hapten 7 (100 mg, 0.36 mmol) in 1 ml of anhydrous DMF was added N-hydroxysuccinamide(49.7 mg, 0.43 mmol) and N,N-dicyclohexylcarbodimide (88.9 mg, 0.43 mmol) and the mixture was stirred at room temperature overnight. The white precipitate of urea formed was filtered off and the filtrate was added dropwise to a solution of BSA (200 mg) in 10 ml of 0.05M phosphate buffer, pH 8.5. The mixture was then stirred overnight at room temperature. The solution was dialysed against distilled water for 20 hours (3 changes) and freeze dried.

By MALDI-TOF (see FIG. 4 of the accompanying drawings), a major signal was present in immunogen 7 which indicates an average protonated mass at mz 68,118. The signals observed at 34,006 and 136,475 are consistent with the major observed component in the doubly charged and dimer forms, respectively. These data suggest that an average of 7.2 molecules of hapten have been conjugated per molecule of BSA.

Example-9

Conjugation of Hapten 7 to HRP 10 mg EDC hydrochloride was dissolved in 800 µl of water and immediately added to a solution of 2 mg of hapten 7 in 200 µl of DMF. After mixing, this solution was added to HRP (20 mg) in 1 ml of water. N-hydroxysulfo-succinimide(5 mg) was immediately added and the reaction mixture was incubated, with stirring, overnight at room temperature. Excess derivative was removed by desalting with 2 PD-10 columns (Pharmacia Biotech) in series, pre-equilibrated with phosphate buffered saline, pH7.2 (PBS). The hapten-HRP conjugate was then dialysed overnight against 10 L of PBS at 4° C.

Example-10

Conjugation of Hapten 9 to HRP 1 ml of a 21 mg/ml solution of sodium periodate was added slowly to HRP (20 mg) in 1 ml of water. The resulting solution was stirred for 20 minutes at room temperature, in the dark, and dialysed against 1 mM acetate buffer, pH 4.5, overnight at 4° C., in the dark. Hapten 9 (2 mg) dissolved in 200 µl DMF was added slowly to the activated enzyme and the reaction mixture was incubated, with stirring, for 2 hours at room temperature, in the dark. Excess derivative was removed by desalting with 2 PD-10 columns (Pharmacia Biotech) in series, pre-equilibrated with phosphate buffered saline, pH7.2(PBS). The hapten-HRP conjugate was then dialysed overnight against 10 L of PBS at 4° C., in the dark.

Example-11

Preparation of HRP-bromoacetylglycine

To a solution of HRP (1 g) in 0.1M borate buffer (pH8.5, 45 ml), protected from light and cooled to 0° C., was added dropwise N-succinimidyl bromoacetylglycine (0.375 mg, 0.13 mmol) in DMF (5 ml). During the addition, the pH was maintained at 8. After complete addition, the pH of the solution was stabilized at 8 and the solution was stirred in the dark at 0° C. for 1 hour. The solution was neutralised to pH 7 and dialyzed overnight at 4° C. against distilled water once and PBS, pH7.2, once.

Example-12

Conjugation of Hapten 10 to Bromoacetylglycine Modified HRP.

10 mg of Hapten 10 was dissolved in 0.5 ml of a 0.12 M solution of potassium carbonate (80% methanol/20% water). The resulting solution was set for 10 minutes in the dark at room temperature. 1 ml of 50 mM phosphate buffer, pH 7, was added to the solution to stop the reaction and the pH adjusted to 7.0–7.5 by addition of 0.1 M HCl. 300 ml of this solution was added dropwise to a solution of bromoacetylglycine modified HRP (20 mg in 1 ml of water) and the mixture was stirred in the dark overnight at 4° C. The hapten-HRP conjugate obtained was purified using two PD10 columns (Pharmacia Biotech), eluted with PBS, pH 7.2, and dialysed overnight against water at 4° C.

Example-13

Preparation of Antibodies Raised Against the Immunogen of Example 8-Immunogen 7

An aqueous solution of the immunogen prepared in Example 8 was formulated with Freund's Complete Adjuvant (FCA) to form an emulsion consisting of 2 mg/ml immunogen in 50% (v/v) FCA. Two sheep were immunised with this emulsion, 0.25 ml being subcutaneously injected at each of 4 sites in the flank of each animal. Subsequent immunisations (boosts) contained 1 mg/ml immunogen emulsified in 50% (v/v) Freund's Incomplete Adjuvant (FIA) and were administered in the same manner at monthly intervals for 1 year. Blood sampling took place 7 to 14 days after each boost. Each sample was processed to produce antiserum that was further purified by caprylic acid and ammonium sulfate precipitation to yield an immunoglobulin G (IgG) fraction. The IgG fraction was evaluated by competitive microtiter plate assay, as described below.

Example-14

Development of Competitive ELISAs for MDMA

The wells of an enhanced binding 96 well polystyrene microtiter plate were coated with the IgG fraction of the antiserum raised to Immunogen 7 (Example 8), diluted in 10 mM Tris, pH8.5 (125 µl/well). The appropriate antibody coating dilution was determined using standard ELISA chequerboard techniques. The plate was incubated for 2 hours at 37° C., washed 4 times with Tris buffered saline containing Tween 20 (TBST) and tapped dry. Standard solutions of MDMA were prepared in TBST at 0, 1, 10, 50, 100, 250, 500 and 1000 ng/ml and 25 µl of each was added to the appropriate wells (FIG. 2). Conjugates (detection reagents)-hapten 7-HRP (Example 9) and hapten 10-HRP (Example 12)—were diluted in Tris buffer, pH7.2, containing EDTA, D-mannitol, sucrose, thimerosal and BSA, appropriate dilutions being determined by standard ELISA chequerboard techniques, and 100 µl of each was added to the appropriate wells (FIG. 2). The plate was incubated at 37° C. for 2 hours. Excess unbound conjugate was removed by washing 6 times over a 10 minute period with TBST.

125 µl of tetramethylbenzidine (TMB) substrate solution was added to each well of the plate which was then incubated for 15 to 20 minutes in the dark at room temperature. The reaction was terminated by addition of 125 µl 0.2 M $H_2SO_4$ to each well. The absorbance was then measured at 450 nm using a microtiter plate reader. The data generated in each assay is presented in Table 1 below.

TABLE 1

Data generated from competitive microtiter plate assays for MDMA employing antiserum raised to immunogen 7 (Example 8) and conjugate 7 (hapten 7-HRP) (Example 9) and conjugate 10 (hapten 10-HRP) (Example 12) as detection reagents.

| Standard Concentration | Conjugate 7 | | Conjugate 10 | |
|---|---|---|---|---|
| ng/ml | $A_{450}$ | % $B/B_0$ | $A_{450}$ | % $B/B_0$ |
| 0 | 2.470 | 100 | 2.37 | 100 |
| 1 | 2.060 | 83.4 | 2.041 | 86.1 |
| 10 | 1.432 | 58 | 1.405 | 59.3 |
| 50 | 0.857 | 34.7 | 0.815 | 34.4 |
| 100 | 0.642 | 26 | 0.671 | 28.3 |
| 250 | 0.393 | 15.9 | 0.465 | 19.6 |
| 500 | 0.269 | 10.9 | 0.341 | 14.4 |
| 1000 | 0.185 | 7.5 | 0.213 | 8.97 |
| $IC_{50}$ | | 17 | | 23.6 |

$A_{450}$ = absorbance at 450 nm
B = absorbance at 450 nm at xng/ml standard concentration
$B_0$ = absorbance at 450 nm at 0 ng/ml standard concentration
$IC_{50}$ = standard concentration which produces 50% B/B0

Example-15

Cross Reactivity of MDMA Competitive ELISAs

In order to determine the specificity of the MDMA competitive ELISAs, standard solutions of potential cross-reactants MDEA, MDA, d-amphetamine, (+)-methamphetamine, (+)-ephedrine, (−)-ephedrine, (+)-pseudoephedrine, (−)-pseudoephedrine and 1-amphetamine were prepared in TBST at 0, 500, 1000, 5000, 10000, 25000, 50000 and 100000 ng/ml. Employing each series of standards in the MDMA competitive ELISAs, calibration curves were generated and these were used to determine the cross-reactivity of the immunoassays with these drugs. The results of this study are presented in Table 2, cross-reactivity being calculated according to the following formula:

$$\% \ CR = IC50_{MDMA}/IC50_{CR} \times 100$$

Where % CR is the percentage cross-reactivity, $IC50_{MDMA}$ is the concentration of MDMA that causes 50% displacement of signal and $IC50_{CR}$ is the concentration of potential cross-reactant, for which % CR is being evaluated, that causes 50% displacement of signal.

It is evident from the results that the MDMA assays exhibit high levels of cross-reactivity with MDEA, lower levels of cross-reactivity with MDA and very low levels of cross-reactivity with d-amphetamine and (+)-methamphetamine. Hence, the MDMA competitive ELISAs are highly specific for MDMA and other methylenedioxy analogs.

TABLE 2

Cross reactivity of the MDMA competitive ELISA

| Trial | Cross-Reactant | Antiserum to immunogen 7 Hapten 7-HRP | |
|---|---|---|---|
| | | IC50 (ng/ml) | % CR |
| 1 | MDMA | 17 | 100 |
| | MDA | 300 | 5.7 |
| | d-Amphetamine | 52199 | 0.03 |
| | (+)-Methamphetamine | 11138 | 0.15 |
| | (+)-Ephedrine | >100000 | <0.017 |
| | (−)-Ephedrine | >100000 | <0.017 |
| | (+)-Pseudoephedrine | >100000 | <0.017 |
| | (−)-Pseudoephedrine | >100000 | <0.017 |
| 2 | MDMA | 30 | 100 |
| | MDEA | 15 | 200 |
| | 1-Amphetamine | >30000 | <0.1 |

The invention claimed is:

1. An immunogen of the following structural formula:

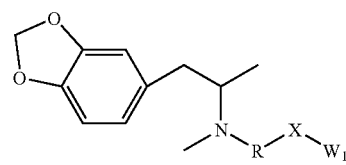

wherein a crosslinker comprises —R—X—, wherein R is a first bivalent group and X is a second bivalent group, and wherein $W_1$ is an antigenicity-conferring carrier material.

2. The immunogen of claim 1, wherein R comprises:

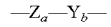

wherein Z is selected from the group consisting of a substituted or unsubstituted, straight or branched chain, saturated or unsaturated alkylene moiety and a substituted or unsubstituted arylene moiety; Y is a substituted or unsubstituted, straight or branched chain, saturated or unsaturated alkylene moiety; a is 0 or 1 and b is 0 or 1, with the proviso that a and b cannot both be 0.

3. The immunogen of claim 2, wherein Z is a substituted or unsubstituted phenylene moiety.

4. The immunogen of claim 2, wherein b is 0, a is 1 and Z is a $C_{1-6}$, substituted or unsubstituted, straight or branched chain, saturated or unsaturated alkylene moiety.

5. The immunogen of claim 4, wherein Z is a $C_{3-4}$ unsubstituted, straight chain, saturated alkylene moiety.

6. The immunogen of claim 1, wherein X is selected from the group consisting of a carboxylic acid or an ester thereof, an amine, a maleimide, a halocarboxylic acid or an ester thereof, a thiocarboxylic acid or an ester thereof, an aldehyde, a pyridyldithio and a vinylsulphone moiety.

7. The immunogen of claim 6, wherein X is selected from the group consisting of a carboxylic acid (—COOH), an amine (—NH₂) and a thiocarboxylate ester (—S—CO—CH₃).

8. The immunogen of claim 1, wherein the carrier material is selected from the group consisting of a protein, a protein fragment, a synthetic polypeptide and a semi-synthetic polypeptide.

9. Antibodies raised against the immunogen of claim 1, the antibodies having specificity for MDMA and other methylenedioxy analogs.

10. The antibodies of claim 9, wherein the antibodies bind a methylenedioxy structural epitope.

11. A process of preparing the antibodies according to claim 9, the process comprising the steps of immunising an animal by repeated administration of the immunogen of claim 1, and collecting the resulting serum from the immunised animal.

12. The process of claim 11, the process comprising the steps of immunising a vertebrate animal by repeated administration of the immunogen of claim 1, and collecting the resulting serum from the immunised animal.

13. The process of claim 11, the process comprising the steps of immunising a mammalian animal by repeated administration of the immunogen of claim 1, and collecting the resulting serum from the immunised animal.

14. A conjugate of the following structural formula:

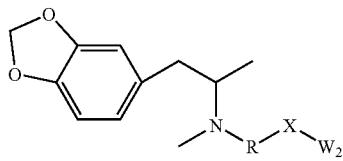

wherein a crosslinker comprises —R—X—, wherein R is a first bivalent group and X is a second bivalent group, and wherein $W_2$ is a detectable labelling agent.

15. The conjugate of claim 14, wherein R comprises:

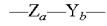

wherein Z is selected from the group consisting of a substituted or unsubstituted, straight or branched chain, saturated or unsaturated alkylene moiety and a substituted or unsubstituted arylene moiety; Y is a substituted or unsubstituted, straight or branched chain, saturated or unsaturated alkylene moiety; a is 0 or 1 and b is 0 or 1, with the proviso that a and b cannot both be 0.

16. The conjugate of claim 15, wherein Z comprises a substituted or unsubstituted phenylene moiety.

17. The conjugate of claim 15, wherein b is 0, a is 1 and Z is a $C_{1-6}$, substituted or unsubstituted, straight or branched chain, saturated or unsaturated alkylene moiety.

18. The conjugate of claim 17, wherein Z is a $C_{3-4}$ unsubstituted, straight chain, saturated alkylene moiety.

19. The conjugate of claim 14, wherein X is selected from the group consisting of a carboxylic acid or an ester thereof, an amine, a maleimide, a halocarboxylic acid or an ester thereof, a thiocarboxylic acid or an ester thereof, an aldehyde, a pyridyldithio and a vinylsulphone moiety.

20. The conjugate of claim 19, wherein X is selected from the group consisting of a carboxylic acid (—COOH), an amine (—NH$_2$) and a thiocarboxylate ester (—S—CO—CH$_3$).

21. The conjugate of claim 14, wherein the labelling agent is selected from the group consisting of an enzyme, a luminescent substance and a radioactive substance; or a mixture thereof.

22. A method for detecting or determining MDMA and its methylenedioxy analogs in a sample, the method comprising contacting the sample with at least one conjugate of claim 14, and with at least one antibody of claim 9; detecting, or determining the quantity of, bound conjugate; and deducing from a calibration curve the presence of, or the amount of, MDMA and its methylenedioxy analogs in the sample.

23. A method for detecting or determining MDMA and its methylenedioxy analogs in a sample, the method comprising contacting the sample with at least one conjugate of claim 15, and with at least one antibody of claim 10; detecting, or determining the quantity of, bound conjugate; and deducing from a calibration curve the presence of, or the amount of, MDMA and its methylenedioxy analogs in the sample.

24. A kit for detecting or determining MDMA and its methylenedioxy analogs, the kit including at least one conjugate of claim 14, and at least one antibody of claim 9.

25. A kit for detecting or determining MDMA and its methylenedioxy analogs, the kit including at least one conjugate of claim 15, and at least one antibody of claim 10.

* * * * *